United States Patent
Whipple et al.

(10) Patent No.: US 10,588,753 B2
(45) Date of Patent: Mar. 17, 2020

(54) CORONAL CORRECTION INTRAVERTEBRAL IMPLANT

(71) Applicant: WHIPPLE BETZ SPINE DEVELOPMENT PARTNERSHIP, Nashua, NH (US)

(72) Inventors: Dale Whipple, Nashua, NH (US); Randal Roberts Betz, Ocean City, NJ (US); Dustin Whipple, Mount Airy, MD (US)

(73) Assignee: WHIPPLE BETZ SPINE DEVELOPMENT PARTNERSHIP, Nashua, NH (US)

( * ) Notice: Subject to any disclaimer, the term of this patent is extended or adjusted under 35 U.S.C. 154(b) by 0 days.

(21) Appl. No.: 15/404,129

(22) Filed: Jan. 11, 2017

(65) Prior Publication Data

US 2018/0333269 A1    Nov. 22, 2018

(51) Int. Cl.
| | |
|---|---|
| *A61F 2/44* | (2006.01) |
| *A61B 17/86* | (2006.01) |
| *A61F 2/46* | (2006.01) |
| *A61B 17/80* | (2006.01) |
| *A61B 17/70* | (2006.01) |
| *A61F 2/30* | (2006.01) |

(52) U.S. Cl.
CPC .............. *A61F 2/442* (2013.01); *A61B 17/86* (2013.01); *A61F 2/44* (2013.01); *A61B 17/7059* (2013.01); *A61B 17/80* (2013.01); *A61F 2/4611* (2013.01); *A61F 2002/30515* (2013.01); *A61F 2002/30538* (2013.01); *A61F 2002/30578* (2013.01)

(58) Field of Classification Search
CPC ................... A61F 2/442; A61F 2/4425; A61F 2002/4435; A61F 2002/444; A61F 2002/4445; A61F 2002/445; A61F 2/4455; A61F 2002/4475
USPC ..................... 606/246–249; 623/17.11–17.16
See application file for complete search history.

(56) References Cited

U.S. PATENT DOCUMENTS

| | | | |
|---|---|---|---|
| 6,623,484 B2 * | 9/2003 | Betz | A61B 17/7044 606/279 |
| 7,833,245 B2 | 11/2010 | Kaes | |
| 8,097,037 B2 | 1/2012 | Serhan | |
| 8,545,567 B1 * | 10/2013 | Krueger | A61F 2/442 623/17.16 |
| 2013/0274810 A1 * | 10/2013 | Fraser | A61B 17/7059 606/279 |

OTHER PUBLICATIONS

Betz RR; Cunningham B; Selgrath C; Drwery T; Sherman MC: Preclinical testing of a wedge-rod system for fusionless correction of scoliosis. Spine (Phila Pa 1976) 28(20S):S275-S278, 2003, 4 pgs., Philadelphia PA, US.

(Continued)

*Primary Examiner* — Julianna N Harvey
*Assistant Examiner* — Christina Negrelli Rodriguez
(74) *Attorney, Agent, or Firm* — John Brooks Law LLC; John J. Brooks, III

(57) ABSTRACT

An implant composed of a plurality of parts placed within a vertebral body such that the vertebral body can be displaced, altering the angle between the superior endplate and the inferior endplate resulting in correction of the vertebral alignment in the coronal plane.

14 Claims, 5 Drawing Sheets

(56) References Cited

OTHER PUBLICATIONS

Betz RR; Mulcahey MJ: New surgical treatments for scoliosis: vertebral body stapling and wedge osteotomies. Viewpoint, Shriners Hospitals for Children, www.shrinershq.org, Sep. 2001, as downloaded from www.SpineUniverse.com on Oct. 15, 2018, 4 pgs., US.

Didelot, William P.; Kling, Thomas F. Jr.; Lindseth, Richard E.: Anterior Vertebral Osteotomies to Correct Lumbar Scoliosis Without Fusion, Ch. 47. In: Modern Anterior Scoliosis Surgery (Lenke, L; Betz, R.; Harms, J., eds.), Thieme Medical Publishers, 2004, pp. 693-706, 7 pgs. (2 pgs. per sheet), New York, US.

McCarthy, Kevin P.; Chafetz, Ross S.; Mulcahey, Mary Jane; Frisch, Richard F.; D'Andrea, Linda P.; Betz, Randal R.: Clinical Efficacy of the Vertebral Wedge Osteotomy for the Fusionless Treatment of Paralytic Scoliosis, Spine, vol. 35, No. 4, pp. 403-410, 2010, Lippincott Williams & Wilkins, 8 pgs., Philadelphia PA, US.

Guille, James T.; Betz, Randal R.; Balsare, Rohinton K.; Mulcahey, M. J.; D'Andrea, Linda P.; Clements, David H.: The Feasibility, Safety, and Utility of Vertebral Wedge Osteotomies for the Fusionless Treatment of Paralytic Scoliosis, Spine, vol. 28, No. 20S, pp. S266-S274, 2003, Lippincott Williams & Wilkins, 9 pgs., Philadelphia PA, US.

James Guille, The Feasibility, Safety, and Utility of Vertebral Wedge Osteotomies for the Fusionless Treatment of Paralytic Scoliosis Spine vol. 28 No. 20s pp. S266-S274 2003 Lippincott Williams & Wlkins, Inc.

Kevin McCarthy, Clinical Efficacy of the Vertebral Wedge Osteotomy for the Fusionless Treatment of Paralytic Scoliosis Spine vol. 35 No. 4 pp. 403-410 2010 Lippincott, Williams & Wilkins, Inc.

Yang, Andres, Non-Final Office Action for co-pending U.S. Appl. No. 15/402,112, dated Aug. 29, 2018, 9 pgs., USPTO, Alexandria VA, USA.

\* cited by examiner

CORONAL CORRECTION INTRAVERTEBRAL IMPLANT

CROSS REFERENCE TO RELATED APPLICATION

This application claims the benefit of application Ser. No. 62/387,763 filed Jan. 4, 2016.

BACKGROUND OF THE INVENTION

1. Field of the Invention

A method for a coronal correction intravertebral implant.

An apparatus for a coronal correction intravertebral implant.

2. Description of the Prior Art

Surgical treatment for scoliosis, a three-dimensional deformity of the thoracic and/or lumbar spine, developed in the 20$^{th}$ century. Instrumentation to assist with correction began to be developed in the 1950s with the Harrington rod and hook system [1]. While this was successful in moderately correcting the coronal deformity, it lacked the ability to correct rotation and the sagittal plane deformity. In the mid-1980s, new rod-hook multisegmented fixation systems began to be developed. This included the Luque segmental spinal instrumentation system [2], the Cotrel-Dubousset system [3], and the TSRH system [4].

Further significant advances developed in the 1990s and early 2000s with the use of pedicle screws attaching to rod systems. This allowed much more advanced correction of all three dimensions of the scoliosis deformity.

In the late 1970s, 80s, and 90s, anterior instrumentation for correction of spine deformity was promoted. These anterior techniques (including Zielke instrumentation [5]) involved removing the intervertebral discs, inserting bone graft into the discs, and/or using structural cages, vertebral body screws (either single or double), and rod systems.

All of these posterior and anterior systems were developed to correct the three dimensions of the spinal deformity but required fusion of all the instrumented vertebral segments. In the late 1990s and 2000s, a technique of wedge osteotomies of the vertebral body, insertion of an intravertebral body spacer, and temporary rod fixation was developed [6, 7]. The rod was then removed after the vertebral body osteotomies had healed, allowing retained motion of these segments.

SUMMARY OF THE INVENTION

An implant composed of a plurality of parts is placed within a vertebral body such that the vertebral body can be displaced, altering the angle between the superior endplate and the inferior endplate resulting in correction of the vertebral alignment in the coronal plane.

Advantages of the Invention

The invention in its broadest aspect utilizes an implant to correct spinal misalignment resulting in correction of the spine in the coronal plane,

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENT

Figure 1:
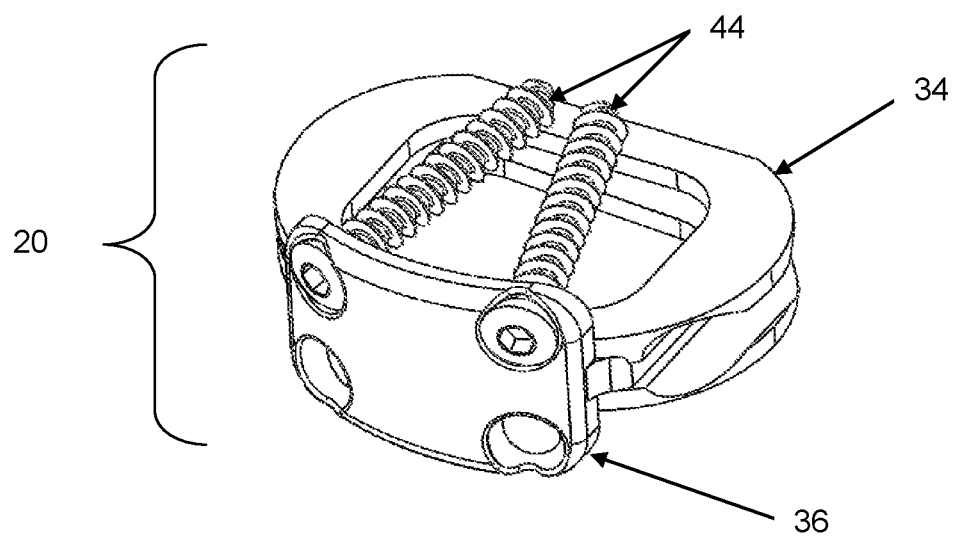
FIG. 1 is an isometric view of the implant
Figure 2A:
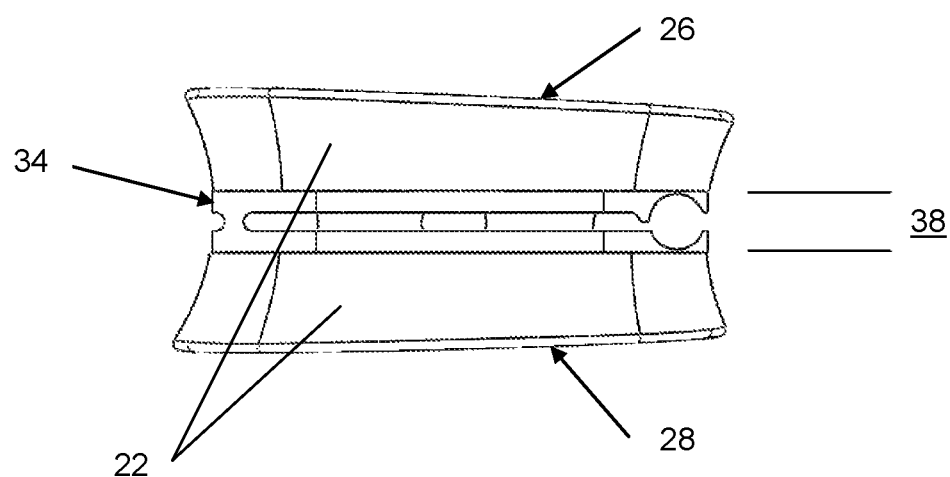
FIG. 2 shows the vertebral body
FIG. 2a Insertion of cage
FIG. 2b Cage displaced
Figure 2B:
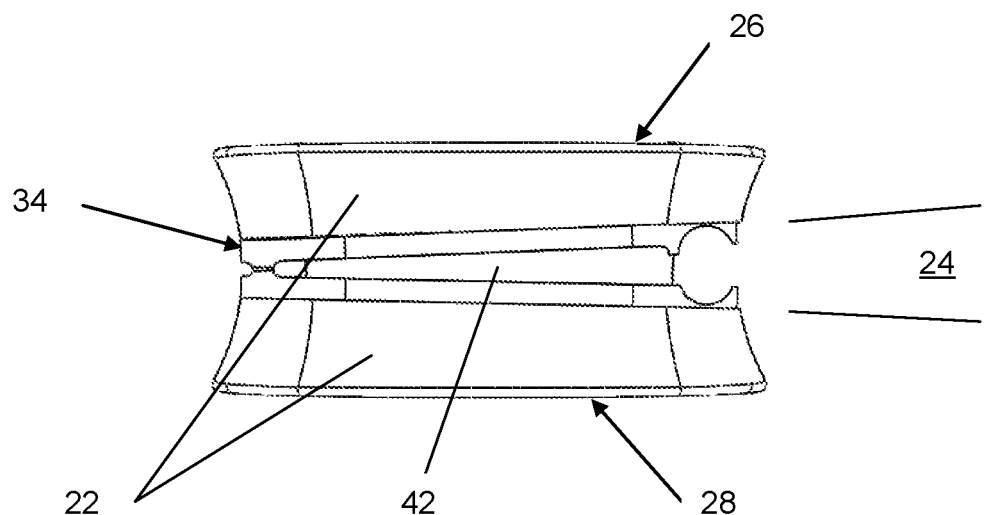
Figure 3:
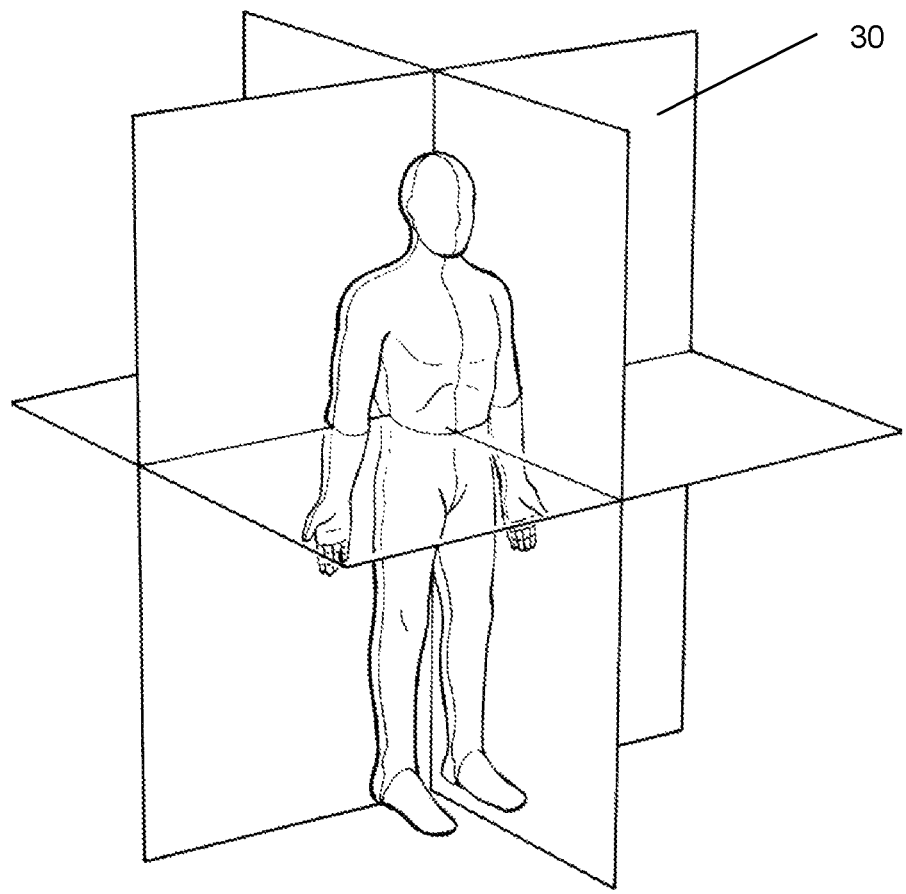
FIG. 3 shows the coronal plane
Figure 4A:
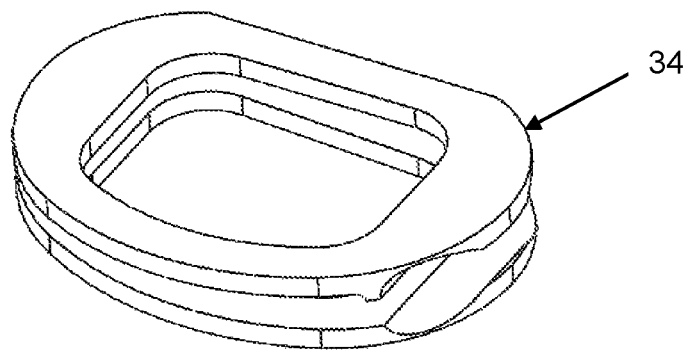
FIG. 4 shows the plurality of parts of the implant
FIG. 4a Cage
FIG. 4b Plate
Figure 4B:
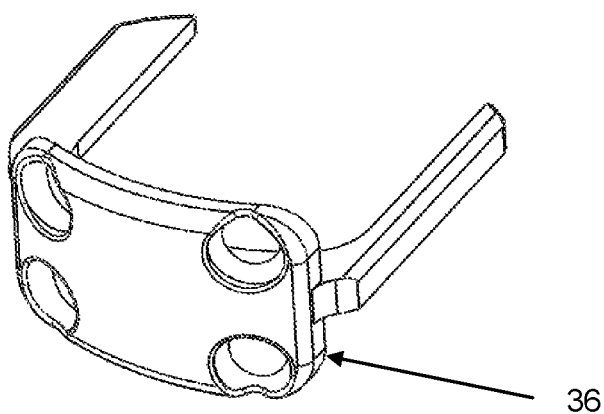
Figure 5:
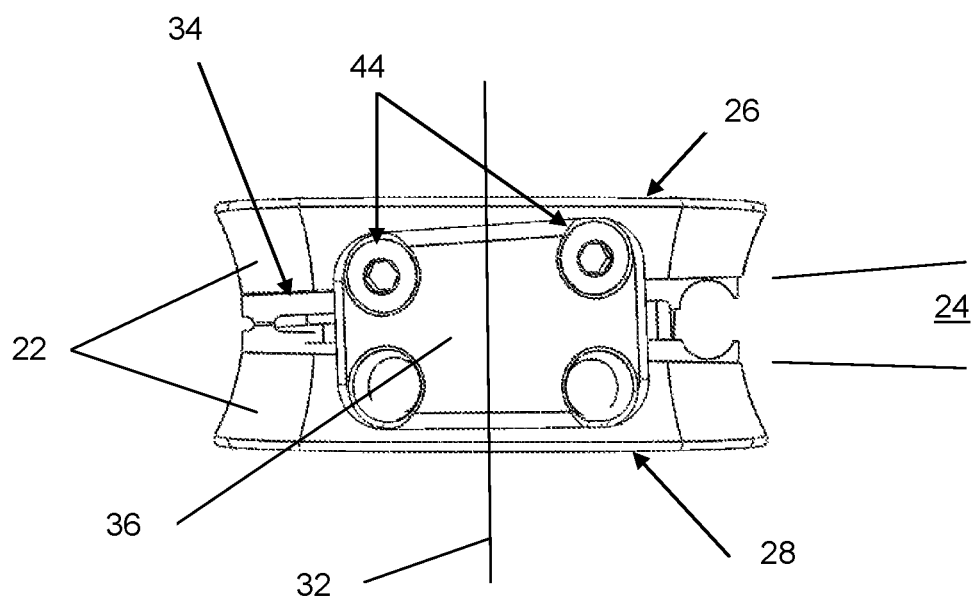
FIG. 5 is the implant in a vertebral body

Referring to the Figures, wherein like numerals indicate corresponding parts throughout the several views, a method for a coronal correction intravertebral implant (20).

An implant (20) composed of a plurality of parts is placed within a vertebral body (22) such that the vertebral body (22) can be displaced altering the angle (24) between the superior endplate (26) and the inferior endplate (28) in the coronal plane (30) resulting in correction of the vertebral bodies (22) into vertical alignment (32) in the coronal plane (30). In the preferred embodiment the parts are a cage (34) and a plate (36). Cutting a slot laterally (38) in the vertebral body (22) allows insertion of the cage (34). The cage (34) is displaced on one end altering the angle (24) between the superior endplate and the inferior endplate (28) of the vertebral body (22). Bone graft (40) can be placed in the void (42) created by the displacement. The plate (36) is inserted into the cage (34) to preserve the angle (24) and is secured by screws (44) into the vertebral body (22).

Many modifications and variations of the present invention are possible in light of the above teachings and may be practiced otherwise than as specifically described while within the scope of the appended claims. In some claims, that which is prior art in the claims precedes the novelty set forth in the "characterized by" clause. In some claims, the novelty is meant to be particularly and distinctly recited in the "characterized by" clause whereas the antecedent recitations merely set forth the old and well-known combination in which the invention resides. In some claims, these antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

| ELEMENT LIST | |
| --- | --- |
| Element Symbol | Element Name |
| 20 | implant |
| 22 | vertebral body |
| 24 | angle |
| 26 | superior endplate |
| 28 | inferior endplate |
| 30 | coronal plane |
| 32 | vertical alignment |
| 34 | cage |
| 36 | plate |
| 38 | slot laterally |
| 42 | void |
| 44 | screws |

What is claimed is:

1. A spinal surgical prosthesis implant (20) for placement within a lateral slot (38) of a single deformed vertebral body (22) having a superior endplate (26) and an inferior endplate (28), said spinal surgical prosthesis implant (20) comprising:
   a cage (34) configured to be placed within the lateral slot (38) of the single deformed vertebral body (22);
   said cage (34) further comprising a cage slot;
   a plate (36);
   said plate (36) further comprising multiple prongs configured to be inserted into said cage slot of said cage (34);
   said multiple prongs having dimensions whereby when said cage (34) is surgically placed within the lateral slot (38) of the single deformed vertebral body (22) and said plate (36) is inserted into said cage slot of said cage (34), an angle (24) made by said cage (34) positions the superior endplate (26) of the single deformed vertebral body (22) and the inferior endplate (28) of the single deformed vertebral body (22) to be substantially parallel;
   wherein the angle (24) comprises a difference in an orientation of a superior surface plane defined by a superior surface of said cage (34) and an orientation of an inferior surface plane defined by an inferior surface of said cage (34); and
   wherein said multiple prongs are displaced from each other in a direction substantially parallel to one of the superior surface plane or the inferior surface plane.

2. Said spinal surgical prosthesis implant (20) of claim 1 wherein the positioning of the superior endplate (26) of the single deformed vertebral body (22) and the inferior endplate (28) of the single deformed vertebral body (22) corrects the vertical alignment (32) of the single deformed vertebral body (22).

3. Said spinal surgical prosthesis implant (20) of claim 1 further comprising a plurality of screws (44) configured to secure said plate (36) and said multiple prongs to the single deformed vertebral body (22).

4. Said spinal surgical prosthesis implant (20) of claim 1 wherein the angle (24) made by said cage (34) positions the superior endplate (26) the single deformed vertebral body (22) and the inferior endplate (28) of the single deformed vertebral body (22) to straighten the vertical alignment of the single deformed vertebral body in the coronal plane (30).

5. Said spinal surgical prosthesis implant (20) of claim 1 wherein said multiple prongs comprise a first prong having a set of first dimensions and a second prong having a set of second dimensions that are different than said set of first dimensions whereby the angle (24) made by a displacement of said cage (34) is greater than zero (0) degrees.

6. Said spinal surgical prosthesis implant (20) of claim 1 wherein:
   said cage (34) comprises a hinge defining one hinged side and one other side;
   the other side of said cage (34) is configured to be displaced whereby the displacement of said cage (34) alters the angle (24) whereby the superior endplate (26) of the single deformed vertebral body (22) and the inferior endplate (28) of the single deformed vertebral body (22) are displaced; and
   said multiple prongs comprise at least two prongs having different dimensions whereby when said plate (36) is inserted into said cage slot of said cage (34), the angle (24) made by a displacement of said cage (34) is greater than zero (0) degrees.

7. Said spinal surgical prosthesis implant (20) of claim 6 wherein said hinged side is configured to be positioned on a lateral side of the single deformed vertebral body (22).

8. Said spinal surgical prosthesis implant (20) of claim 6 wherein said other side of said cage (34) is configured to be an open side.

9. Said spinal surgical prosthesis implant (20) of claim 1 further comprising a bone graft configured to be placed in the void (42) created by the positioning of the superior endplate (26) of the single deformed vertebral body (22) and the inferior endplate (28) of the single deformed vertebral body (22).

10. Said spinal surgical prosthesis implant (20) of claim 1 wherein:
    said cage (34) comprises a hinge defining one hinged side and one other side;
    said other side of said cage (34) is configured to be displaced whereby the displacement of said cage (34) alters the angle (24) whereby the superior endplate (26) of the single deformed vertebral body (22) and the inferior endplate (28) of the single deformed vertebral body (22) are displaced;
    said multiple prongs comprise a first prong having a set of first dimensions and a second prong having a set of second dimensions that are different than said set of first dimensions whereby when said plate (36) is inserted into said cage slot of said cage (34), the angle (24) made by a displacement of said cage (34) is greater than zero (0) degrees;
    said spinal surgical prosthesis implant (20) further comprises a plurality of screws (44) configured to secure said plate (36) and said multiple prongs to the single deformed vertebral body (22); and
    said spinal surgical prosthesis implant (20) further comprises a bone graft configured to be placed in the void (42) created by the displacement of the superior endplate (26) of the single deformed vertebral body (22) and the inferior endplate (28) of the single deformed vertebral body (22).

11. Said spinal surgical prosthesis implant (20) of claim 10 wherein said hinged side is configured to be positioned on a lateral side of the single deformed vertebral body (22).

12. Said spinal surgical prosthesis implant (20) of claim 10 wherein said other side of said cage (34) is configured to be an open side.

13. A spinal surgical prosthesis implant (20) for placement within a lateral slot (38) of a single deformed vertebral body (22) having a superior endplate (26) and an inferior endplate (28), said spinal surgical prosthesis implant (20) comprising:
    a cage (34) configured to be placed within the lateral slot (38) of the single deformed vertebral body (22);
    said cage (34) further comprising a cage slot;
    a plate (36);
    said plate (36) further comprising multiple prongs configured to be inserted into said cage slot of said cage (34);
    said multiple prongs having dimensions whereby when said cage (34) is surgically placed within the lateral slot (38) of the single deformed vertebral body (22) and said plate (36) is inserted into said cage slot of said cage (34), an angle (24) made by said cage (34) positions the superior endplate (26) of the single deformed vertebral body (22) and the inferior endplate (28) of the single deformed vertebral body (22) to be substantially parallel;
    wherein the angle (24) comprises a difference in an orientation of a superior surface plane defined by a superior surface of said cage (34) and an orientation of an inferior surface plane defined by an inferior surface of said cage (34);

said cage (34) comprises a hinge defining one hinged side and one other side;

the other side of said cage (34) is configured to be displaced whereby the displacement of said cage (34) alters the angle (24) whereby the superior endplate (26) of the single deformed vertebral body (22) and the inferior endplate (28) of the single deformed vertebral body (22) are displaced; and said multiple prongs comprise at least two prongs having different dimensions whereby when said plate (36) is inserted into said cage slot of said cage (34), the angle (24) made by a displacement of said cage (34) is greater than zero (0) degrees.

14. A spinal surgical prosthesis implant (20) for placement within a lateral slot (38) of a single deformed vertebral body (22) having a superior endplate (26) and an inferior endplate (28), said spinal surgical prosthesis implant (20) comprising:

a cage (34) configured to be placed within the lateral slot (38) of the single deformed vertebral body (22);

said cage (34) further comprising a cage slot;

a plate (36);

said plate (36) further comprising multiple prongs configured to be inserted into said cage slot of said cage (34);

said multiple prongs having dimensions whereby when said cage (34) is surgically placed within the lateral slot (38) of the single deformed vertebral body (22) and said plate (36) is inserted into said cage slot of said cage (34), an angle (24) made by said cage (34) positions the superior endplate (26) of the single deformed vertebral body (22) and the inferior endplate (28) of the single deformed vertebral body (22) to be substantially parallel;

wherein the angle (24) comprises a difference in an orientation of a superior surface plane defined by a superior surface of the cage (34) and the orientation of an inferior surface plane defined by an inferior surface of the cage (34);

said cage (34) comprises a hinge defining one hinged side and one other side;

said other side of said cage (34) is configured to be displaced whereby the displacement of said cage (34) alters the angle (24) whereby the superior endplate (26) of the single deformed vertebral body (22) and the inferior endplate (28) of the single deformed vertebral body (22) are displaced;

said multiple prongs comprise a first prong having a set of first dimensions and a second prong having a set of second dimensions that are different than said set of first dimensions whereby when said plate (36) is inserted into said cage slot of said cage (34), the angle (24) made by a displacement of said cage (34) is greater than zero (0) degrees;

said spinal surgical prosthesis implant (20) further comprises a plurality of screws (44) configured to secure said plate (36) and said multiple prongs to the single deformed vertebral body (22); and said spinal surgical prosthesis implant (20) further comprises a bone graft configured to be placed in a void (42) created by the displacement of the superior endplate (26) of the single deformed vertebral body (22) and the inferior endplate (28) of the single deformed vertebral body (22).

* * * * *